United States Patent
Ferree

(10) Patent No.: US 7,267,688 B2
(45) Date of Patent: Sep. 11, 2007

(54) BIAXIAL ARTIFICIAL DISC REPLACEMENT

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 10/690,889

(22) Filed: Oct. 22, 2003

(65) Prior Publication Data

US 2004/0127991 A1   Jul. 1, 2004

Related U.S. Application Data

(60) Provisional application No. 60/420,169, filed on Oct. 22, 2002.

(51) Int. Cl.
*A61F 2/44* (2006.01)
(52) U.S. Cl. .................................... 623/17.11
(58) Field of Classification Search .. 623/17.11–17.16; 606/60, 61
See application file for complete search history.

(56) References Cited

U.S. PATENT DOCUMENTS

| | | | |
|---|---|---|---|
| 4,759,769 A * | 7/1988 | Hedman et al. | 623/17.13 |
| 5,522,899 A * | 6/1996 | Michelson | 606/61 |
| 6,245,107 B1 | 6/2001 | Ferree | 623/17 |
| 6,371,990 B1 | 4/2002 | Ferree | 623/17.16 |
| 6,454,804 B1 | 9/2002 | Ferree | 623/17.11 |
| 6,602,291 B1 | 8/2003 | Ray et al. | 623/17.11 |
| 2002/0156533 A1 | 10/2002 | Ferree | |
| 2002/0165542 A1 | 11/2002 | Ferree | |
| 2003/0004574 A1 | 1/2003 | Ferree | |
| 2003/0040796 A1 | 2/2003 | Ferree | |
| 2003/0078579 A1 | 4/2003 | Ferree | |

FOREIGN PATENT DOCUMENTS

WO   WO 01/103164 A1   2/2001

\* cited by examiner

*Primary Examiner*—Anuradha Ramana
(74) *Attorney, Agent, or Firm*—Gifford, Krass, Sprinkle, Anderson & Citkowski, PC

(57) ABSTRACT

An artificial disc replacement (ADR) is designed to protect a cushioning component from excessive force. Physical features on the front and back of the ADR enable the device to replicate the normal movements of the spine through predetermined, limited, movements of the endplate components relative to one another. For example, though not limited to these characteristics, the components of the ADR could be dimensioned to allow 15 degrees of flexion, 5 degrees of extension, 5 degrees of lateral bending, and 1-2 mm of translocation. In the preferred embodiment the physical features are axles that extend through overlapping lateral portions associated with the endplate components. A desirable configuration includes a pair of axles, one in the anterior portion and another in the posterior portion, wherein some or all of the axles extend through an oversized aperture that allows the limited relative movement of the endplate components. Alternatively, the anterior and posterior physical features may include mating projections and depressions to permit a desired degree of relative movement.

5 Claims, 4 Drawing Sheets

BIAXIAL ARTIFICIAL DISC REPLACEMENT

REFERENCE TO RELATED APPLICATION

This application claims priority from U.S. Provisional Patent Application Ser. No. 60/420,169, filed Oct. 22, 2002, the entire content of which is incorporated herein by reference.

FIELD OF THE INVENTION

This invention relates generally to artificial disc replacement (ADR) and, in particular, to ADRs including cushioning components to protect the implant from excessive force.

BACKGROUND OF THE INVENTION

Improvements in prosthetic intervertebral disc and joint replacement components, and related surgical procedures, have led to dramatic increases in implant longevity. Many artificial hip and knee components now last for twenty years or more due to improved materials and greater insight into movement, load distribution and wear characteristics.

Many spinal conditions, including degenerative disc disease, can now be treated through artificial disc replacement (ADR), which has several advantages over spinal fusion. The most important advantage of ADR is the preservation of spinal motion. Spinal fusion eliminates motion across the fused segments of the spine. Consequently, the discs adjacent to the fused level are subjected to increased stress, which increases the changes of future surgery to treat the degeneration of the discs adjacent to the fusion.

One of the most important features of an artificial disc replacement (ADR) is its ability to replicate the kinematics of a natural disc. ADRs that replicate the kinematics of a normal disc are less likely to transfer additional forces above and below the replaced disc. In addition, ADRs with natural kinematics are less likely to stress the facet joints and the annulus fibrosus (AF) at the level of the disc replacement. Replicating the movements of the natural disc also decreases the risk of separation of the ADR from the vertebrae above and below the ADR.

In an attempt to replicate natural disc movements various ADR materials have been tried, including hydrogels, metal and rubber. As one example, U.S. Pat. No. 6,602,291 resides in a prosthetic spinal disc nucleus comprising a hydrogel core surrounded by a constraining jacket. The hydrogel core is configured to expand from a dehydrated state to a hydrated state. In the dehydrated state, the hydrogel core has a shape selected to facilitate implantation through an annulus opening. Further, in the hydrated state, the hydrogel core has a shape corresponding generally to a portion of a nucleus cavity, the hydrated shape being different from the dehydrated shape. Upon hydration, the hydrogel core transitions from the dehydrated shape to the hydrated shape.

Unfortunately, the flexibility of the hydrogel and the constraining jacket allow hydrogel ADRs to change shape and extrude through defects in the annulus through which the ADR was inserted, for example. My U.S. Pat. Nos. 6,245,107, 6,371,990, 6,454,804, and published applications WO 01/10316 A1; 20020156533; 20020165542; 20030004574; 20030040796; and 20030078579 are useful in addressing such problems.

Metal and rubber ADRs, on the other hand, also frequently fail at the metal-rubber interface. The rubber fails directly due to high shear stresses or because the rubber separates from the metal. Clearly any improvements in these and other areas would be welcomed by the medical community and by patients undergoing procedures to implant prosthetic components of this kind.

SUMMARY OF THE INVENTION

This invention broadly resides in an ADR that protects a cushioning component from excessive force. In the preferred embodiment, physical features on the front and/or back of the ADR enable the device to replicate the normal movements of the spine through predetermined, limited, movements of the endplate components relative to one another. For example, though not limited to these characteristics, the components of the ADR could be dimensioned to allow 15 degrees of flexion, 5 degrees of extension, 5 degrees of lateral bending, and 1-2 mm of translocation.

In the preferred embodiment the physical features are axles that extend through overlapping lateral portions associated with the endplate components. A desirable configuration includes a pair of axles, one in the anterior portion and another in the posterior portion, wherein some or all of the axles extend through an oversized aperture that allows the limited relative movement of the endplate components. Alternatively, the anterior and posterior physical features may include mating projections and depressions to permit a desired degree of relative movement.

DETAILED DESCRIPTION OF THE INVENTION

Figure 1:
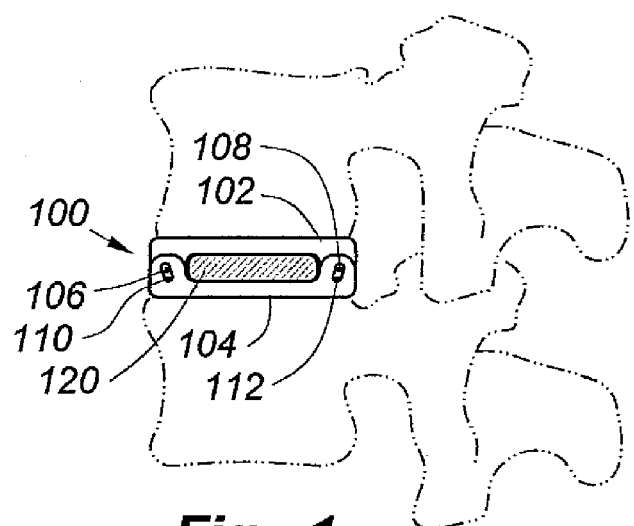
FIG. 1 is a view of the lateral aspect of the spine and an ADR according to the present invention.

FIG. 1 is a view of the lateral aspect of the spine and an ADR according to the invention depicted generally at 100. A top endplate component 102 articulates with a bottom endplate component 104 through axles 106, 108 in the front and back of the ADR. A cushioning component 120 is disposed between the endplate components 102, 104. Holes 110, 112 of the bottom endplate component receive the axles 106, 108 and are sized to allow normal movements of the spine, preferably a limited amount of flexion, extension, lateral bending, and/or translocation. Depending upon the type and degree of desired movement, over-sized holes may be provided on the top endplate component, or both components 102, 104.

The endplate components are preferably made of metal, and the surface of each endplate component adjacent to the vertebrae would preferably incorporate a bone-ingrowth promoting surface of the types known to those skilled in orthopaedic design. The cushion component 120 would likely be an elastomer, though contained hydrogels and other compressible synthetic and natural members may alternatively be used. The invention is not limited in this regard. The cushion component 120 would be held in position between the endplate components 102, 104 by lips around the periphery of the endplate components. As such, the cushioned 102 component would not need to be bonded to the endplate components.

Figure 2:
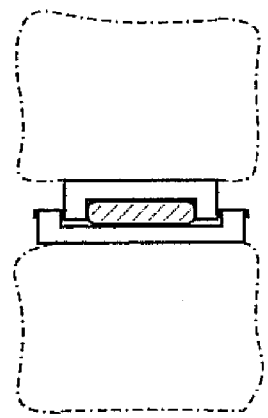
FIG. 2 is a view of the anterior aspect of the spine and the ADR.
Figure 3:
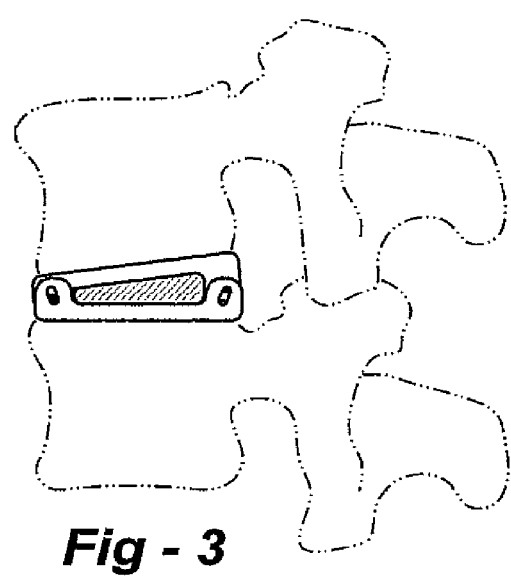
FIG. 3 is a view of the lateral aspect of a flexed spine and the ADR.
Figure 4:
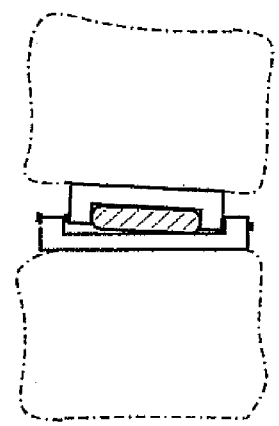
FIG. 4 is a view of the anterior aspect of a spine in lateral bending and the ADR.

FIG. 2 is a view of the anterior aspect of the spine and the ADR. Note that the various components are preferably sized to facilitate lateral bending. FIG. 3 is a view of the lateral aspect of a flexed spine and the ADR, better reveling how the anterior axle travels to the inferior aspect of the hole in the bottom endplate component. The posterior axle travels to the top of the posterior hole in the bottom endplate component. FIG. 4 is a view of the anterior aspect of a spine in lateral bending and the ADR. As discussed above, the top endplate component could impinge against the bottom endplate component after a level of lateral bending such as 5 degrees.

The articulations between the two-endplate components 102,104 limit the forces experienced by the cushion component 120. For example, the cushion component 120 may be protected from excessive shear. The dimensions of the endplate components 102, 104 may further be dimensioned and/or proportioned to protect the cushion component 102 from excessive axial loads. As best seen in FIG. 4, the top and bottom endplate components 102, 104 may be designed to impinge after a certain amount of compression of the cushion component 120. Such impingement between the top and bottom endplate components would also help to protect the axles 106,108. In addition, impingement of the endplate components 102, 104 should help protect the facet joints and remaining annulus fibrosis from excessive force.

Figure 5A:
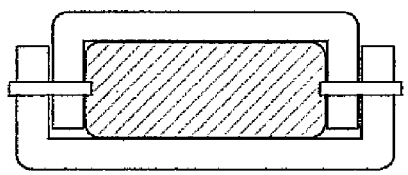
FIG. 5A is a coronal cross section of one configuration wherein four axles connect the endplates.
Figure 5B:
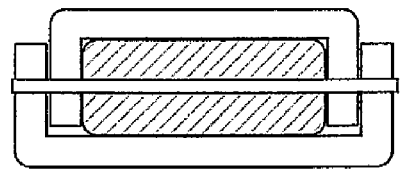
FIG. 5B is a coronal cross section of an alternative embodiment.
Figure 5C:
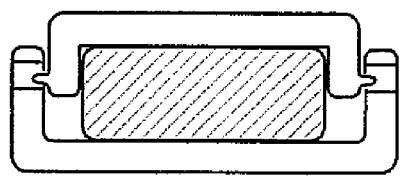
FIG. 5 shows how the component nests in each other.

The axles may or may not extend through the cushion component. FIG. 5A is a coronal cross section of one configuration wherein four axles connect the endplates. FIG. 5B is a coronal cross section of an alternative embodiment wherein two axles connect the endplates. Note that although separate elements are shown for the endplate components and axles, the axles may be integral to one of the components, particularly the component that nests in the other, as shown in FIG. 5C.

Figure 6B:
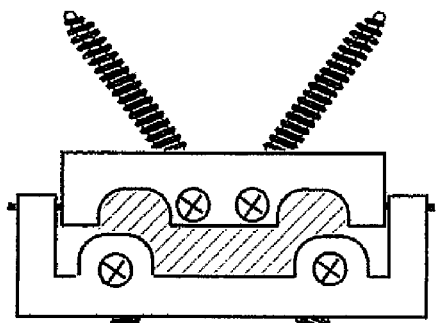
FIG. 6B is a frontal view with an emphasis on screw orientation.
Figure 6A:
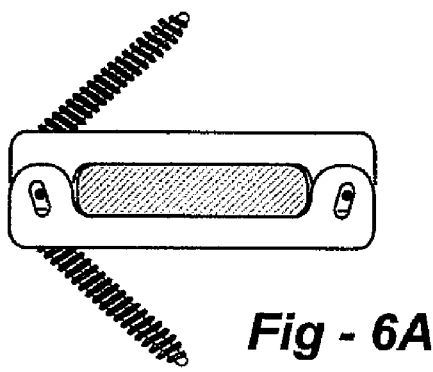
FIG. 6A is a view of the lateral aspect of the ADR with optional screws to fix the ADR to the vertebrae.

FIG. 6A is a view of the lateral aspect of the ADR with optional screws to fix the ADR to the vertebrae. FIG. 6B is a front view. In the preferred embodiments, the ADR would incorporate some mechanism to prevent the screws form backing out.

Figure 7A:
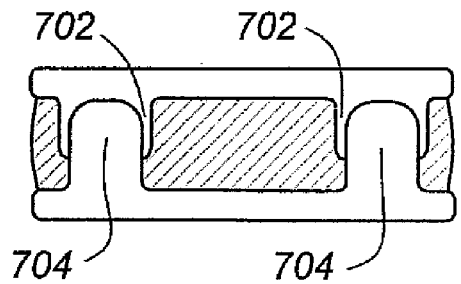
FIG. 7A is a view of the lateral aspect of an alternative embodiment of the ADR.
Figure 7B:
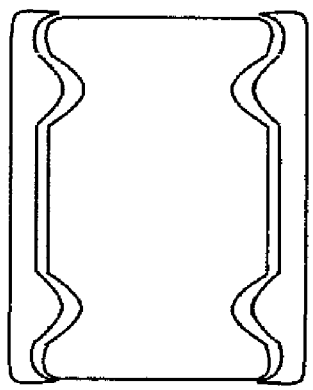
FIG. 7B is a view of the top of the ADR drawn in FIG. 7A.

FIG. 7A is a view of the lateral aspect of an alternative embodiment of the ADR. FIG. 7B is a view of the top of the ADR drawn in FIG. 7A. In this case, hemi-cylindrical projections 702 from the upper endplate articulate with hemi-piston projections 704 form the lower endplate. As described above the articulations between the endplates permit normal spinal movement and cushioning. The endplates also prohibit excessive movements and excessive forces between the endplates.

Figure 8:
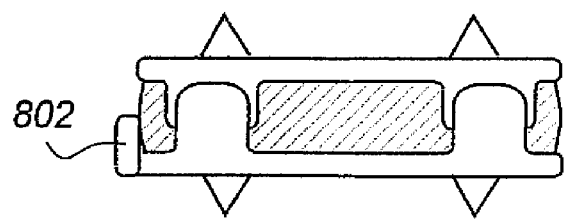
FIG. 8 is a view of the lateral aspect of an alternative embodiment of the ADR drawn in FIG. 7A.

FIG. 8 is a view of the lateral aspect of an alternative embodiment of the ADR drawn in FIG. 7A, including a removable plate 802 associated with the lower endplate allows assembly of the ADR within the disc space. The shape of the endplates, the articulations between the endplates, and the removable plate hold the elastomer in place between the endplates. Again, the elastomer need not be glued to the endplates.

Figure 9A:
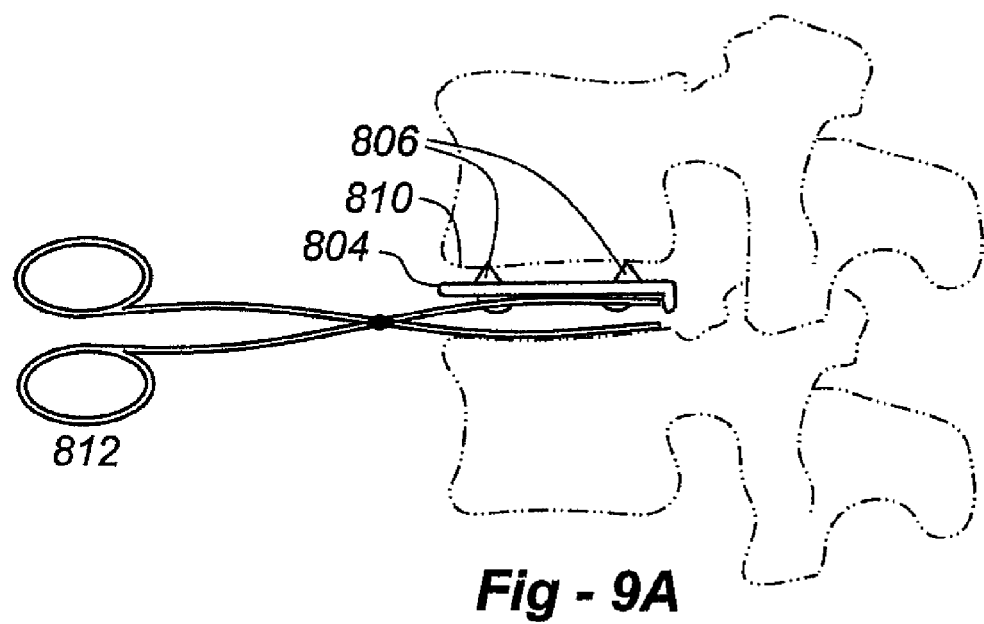
FIG. 9A is a view of the lateral aspect of the spine and the superior endplate of the ADR.
Figure 9B:
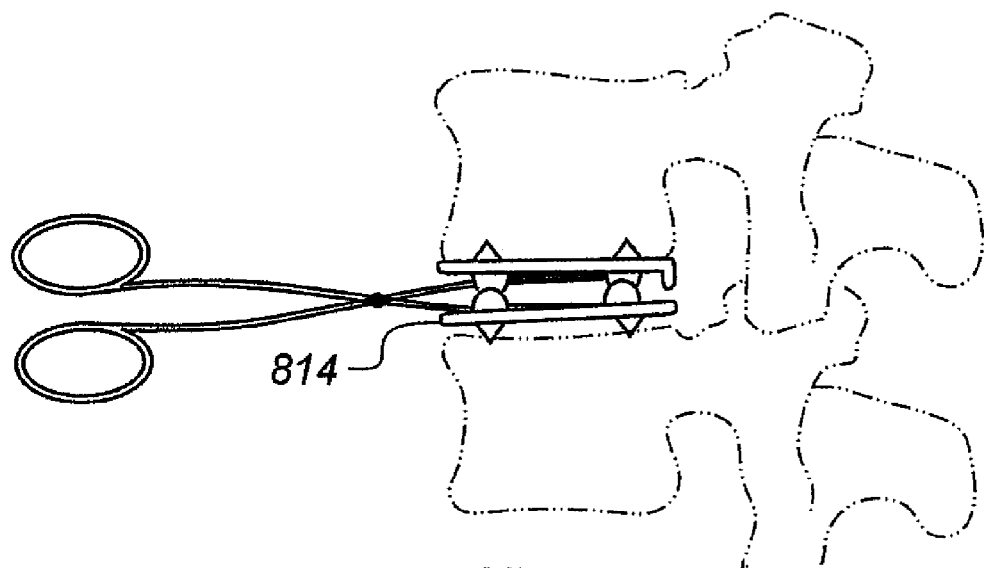
FIG. 9B is a view of the lateral aspect of the spine and the insertion of the inferior endplate.
Figure 9C:
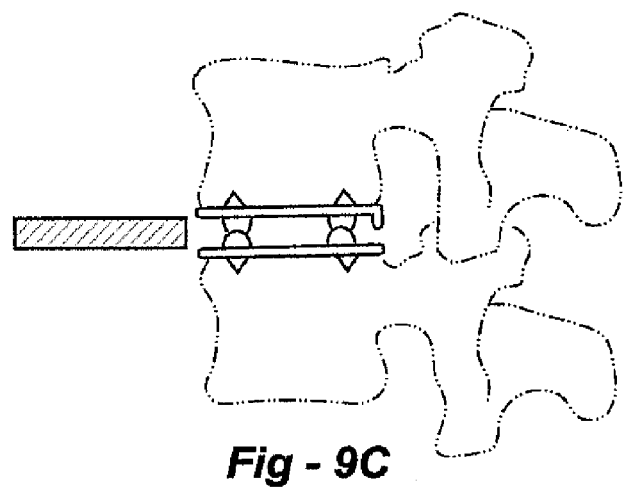
FIG. 9C shows insertion of the elastomeric component.
Figure 9D:
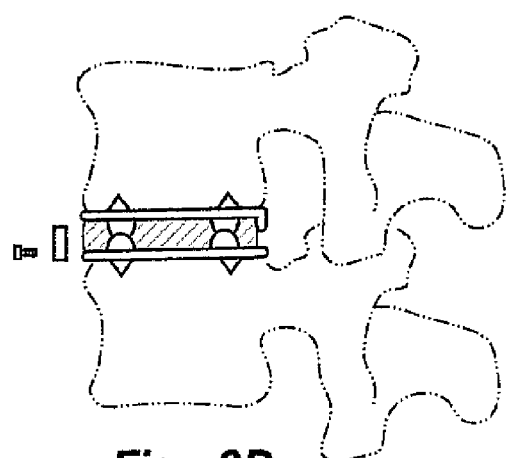
FIG. 9D shows insertion of the anterior plate onto the inferior endplate of the ADR.

FIGS. 9A-9D illustrate an insertion sequence applicable to the ADR drawn in FIG. 8. FIG. 9A is a view of the lateral aspect of the spine and the superior endplate 804 of the ADR. Spikes 806 on the endplate are press fit into the vertebral endplate 810 using a distraction instrument 812. FIG. 9B is a view of the lateral aspect of the spine and the insertion of the inferior endplate 814. The distraction instrument 812 fits into the upper and lower ADR endplates to assure the inferior endplate is properly aligned with respect to the superior endplate of the ADR. FIG. 9C shows insertion of the elastomeric component. FIG. 9D shows insertion of the anterior plate onto the inferior endplate of the ADR. A screw or screws holds the anterior plate on the in inferior endplate of the ADR.

Figure 10A:
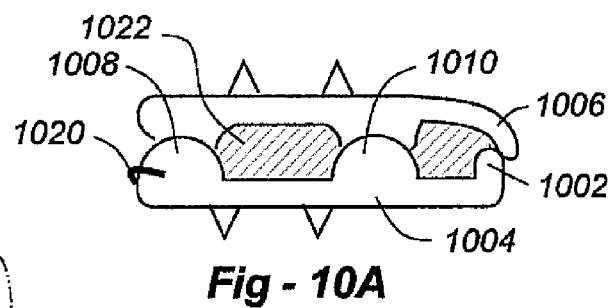
FIG. 10A is a view of the lateral aspect of another embodiment of the present invention.
Figure 10B:
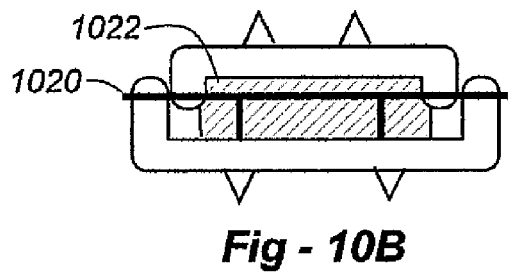
FIG. 10B is a view of the anterior aspect of the device drawn in FIG. 10A.

FIG. 10A is a view of the lateral aspect of another embodiment of the invention. FIG. 10B is a view of the anterior aspect of the device drawn in FIG. 10A. A lip 1002 on the posterior aspect of the inferior endplate 1004 prevents the superior endplate 1006 from sliding forward. The tongue-like projections 1008, 1010 of the superior and inferior endplates cooperate to limit lateral bending, for example to 5 degrees in either direction. The posterior projections form the superior endplate can also limit extension; to 5 degrees, for example. A movable clip 1020 prevents the elastomer 1022 from falling out of the front of the device. The elastomer may have a thin sheet of metal glued to its superior and inferior surfaces. The low friction of the metal sheets would facilitate movement of the elastomer between the endplate components.

Figure 11A:
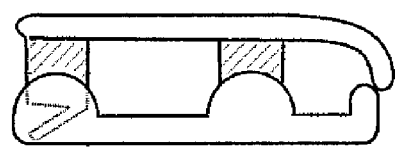
FIG. 11A is a view of the lateral aspect of yet a further alternative embodiment of the ADR.
Figure 11B:
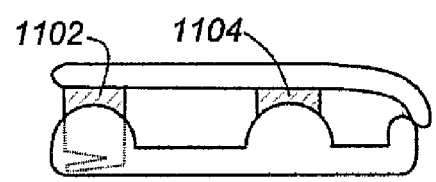
FIG. 11B is a view of the lateral aspect of the device drawn in FIG. 11A.

FIG. 11A is a view of the lateral aspect of yet a further alternative embodiment of the ADR. Projections 1102, 1104 from the superior endplate have extensions. The extensions 1102, 1104 help hold the elastomer in position without interfering with the motion of the two endplate components. The endplate components do not cooperate to limit lateral bending in this embodiment. The dotted line represents the oudine of the portion of the projection that lies within a recess of the projection 1102 from the superior endplate. FIG. 11B is a view of the lateral aspect of the device drawn in FIG. 11A. The projections are drawn in a collapsed position.

I claim:

1. An artificial disc replacement (ADR) configured for placement between two vertebral bodies having a medial-lateral orientation and anterior and posterior portions, the ADR comprising:

opposing superior and inferior endplate components, each fixed to a respective one of the vertebral bodies;

a cushioning component disposed between the opposing endplate components;

a pair of opposing anterior side portions extending downwardly from the superior endplate component, each portion including a hole therethrough;

a pair of opposing posterior side portions extending downwardly from the superior endplate component, each portion including a hole therethrough;

a pair of opposing anterior side portions extending upwardly from the inferior endplate component, each portion including a hole therethrough that overlaps with a respective one of the holes of the opposing anterior side portions extending downwardly from the superior endplate component;

a pair of opposing posterior side portions extending upwardly from the inferior endplate component, each portion including a hole that overlaps with a respective one of the holes of the opposing posterior side portions extending downwardly from the superior endplate component;

one or two rods passing through the overlapping holes of the overlapping anterior side portions;

one or two rods passing through the overlapping holes of the overlapping posterior side portions; and wherein at least some of the rods have cross-sectional areas that are smaller than some of the holes through which they pass, thereby permitting a predetermined, limited, movement of the endplate components relative to one another.

2. The ADR of claim 1, wherein the anterior and posterior side portions permit a predetermined, limited degree of flexion.

3. The ADR of claim 1, wherein the anterior and posterior side portions permit a predetermined, limited degree of extension.

4. The ADR of claim 1, wherein the anterior and posterior side portions permit a predetermined, limited degree of lateral bending.

5. The ADR of claim 1, wherein the anterior and posterior side portions permit a predetermined, limited degree of translocation.

* * * * *